United States Patent
Brosck et al.

(10) Patent No.: US 6,656,491 B1
(45) Date of Patent: Dec. 2, 2003

(54) ACTIVE SUBSTANCE PLASTERS

(75) Inventors: Katharina Brosck, Taubaté (BR); Peter Jauchen, Hamburg (DE); Ulrich Köhler, Hamburg (DE); Peter Himmelsbach, Buxtehude (DE); Matthias Wasner, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/719,114

(22) PCT Filed: Jun. 5, 1999

(86) PCT No.: PCT/EP99/03900

§ 371 (c)(1),
(2), (4) Date: Dec. 7, 2000

(87) PCT Pub. No.: WO99/64082

PCT Pub. Date: Dec. 16, 1999

(30) Foreign Application Priority Data

Jun. 8, 1998 (DE) .......................... 198 25 499

(51) Int. Cl.⁷ ........................ A61F 13/02; A61F 13/00
(52) U.S. Cl. ..................... 424/428; 424/449; 424/443
(58) Field of Search ................ 424/448, 449, 424/443

(56) References Cited

U.S. PATENT DOCUMENTS

| | | | | |
|---|---|---|---|---|
| 4,801,458 A | * | 1/1989 | Hidaka et al. .............. | 424/443 |
| 5,065,752 A | * | 11/1991 | Sessions et al. ........... | 428/304.4 |
| 5,371,128 A | | 12/1994 | Ulman et al. .............. | 524/265 |
| 5,389,168 A | * | 2/1995 | Litchholt et al. ........... | 156/160 |
| 5,660,854 A | | 8/1997 | Haynes et al. ............. | 424/450 |
| 6,143,317 A | | 11/2000 | Himmelsbach et al. ..... | 424/443 |

FOREIGN PATENT DOCUMENTS

| | | | |
|---|---|---|---|
| DE | 37 43 945 | 2/1992 | ............. B01J/4/00 |
| DE | 43 22 334 | 1/1994 | ............. C09J/33/04 |
| DE | 42 24 325 | 2/1994 | ............. A61L/15/58 |
| DE | 43 16 751 | 8/1994 | ............. A61L/15/44 |
| DE | 43 10 012 | 9/1994 | ............. A61L/15/44 |
| DE | 42 37 252 | 10/1994 | ............. C09J/7/02 |
| DE | 43 08 649 | 11/1995 | ............. A61L/15/42 |
| DE | 196 20 109 | 11/1997 | |
| EP | 0 053 936 | 6/1982 | |
| EP | 0 305 756 B1 | * 8/1988 | |
| EP | 0 305 756 | 3/1989 | ............. A61K/9/70 |
| EP | 0 305 757 | 3/1989 | ............. A61L/15/03 |
| EP | 0 305 758 | 3/1989 | ............. A61L/15/58 |
| EP | 0 439 180 | 7/1991 | ............. A61L/15/44 |
| EP | 0 443 759 | 8/1991 | ............. C09J/183/04 |
| EP | 0 452 034 | 10/1991 | ............. C09J/83/04 |
| EP | 0 353 972 | 1/1994 | ............. A61F/13/02 |
| EP | 0 663 431 | 7/1995 | ............. C09J/11/08 |
| EP | 0 914 820 | 5/1999 | |
| FR | 1421732 | 11/1965 | |
| WO | 94/02123 | 2/1994 | ............. A61K/9/70 |
| WO | 96/22083 | 7/1996 | ............. A61K/9/70 |

* cited by examiner

*Primary Examiner*—Thurman K. Page
*Assistant Examiner*—Isis Ghali
(74) *Attorney, Agent, or Firm*—Norris McLaughlin & Marcus

(57) ABSTRACT

Active substance plasters consisting of a backing material and an at least partially applied adhesive composition, characterized in that a component comprising one or more active substances is additionally applied in the form of spun fibres or filaments to the backing material, this component having an at least partly thermoplastic basis.

36 Claims, 3 Drawing Sheets

ACTIVE SUBSTANCE PLASTERS

Figure 1:
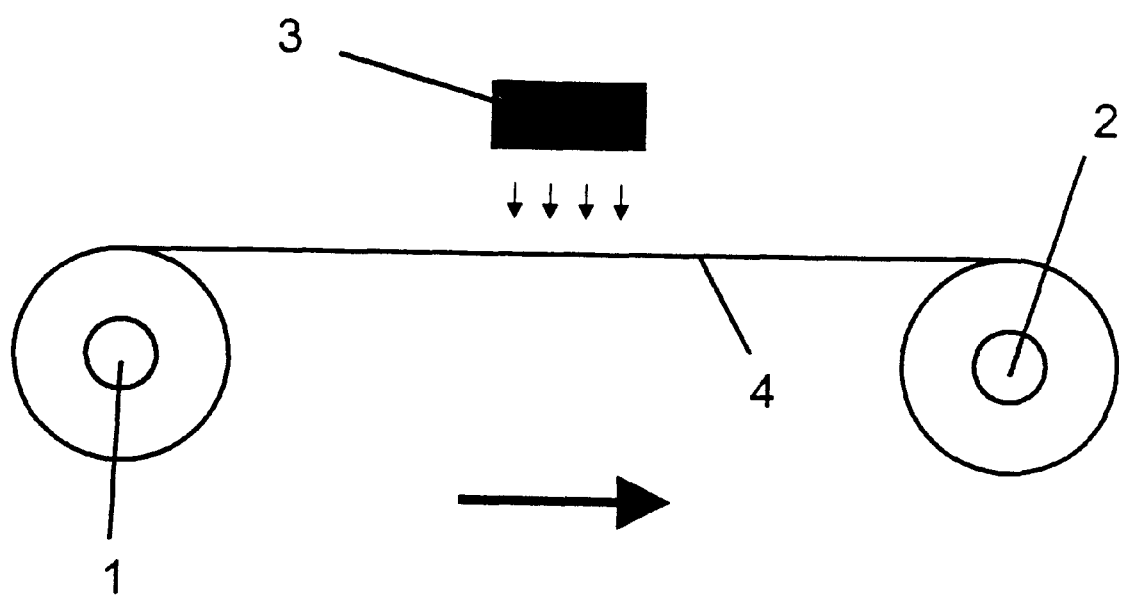
Figure 2:
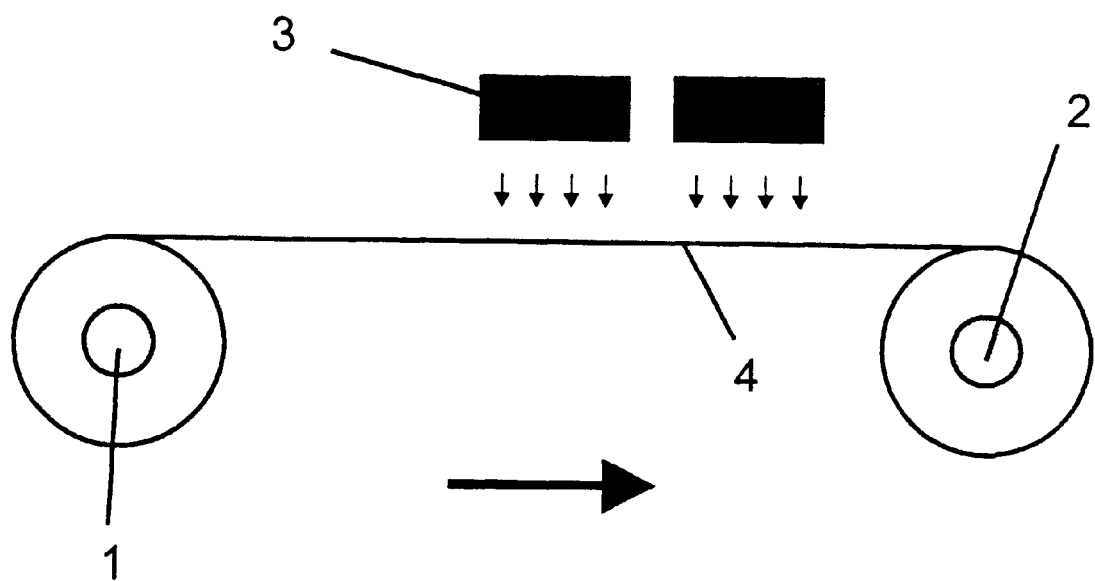
Figure 3:
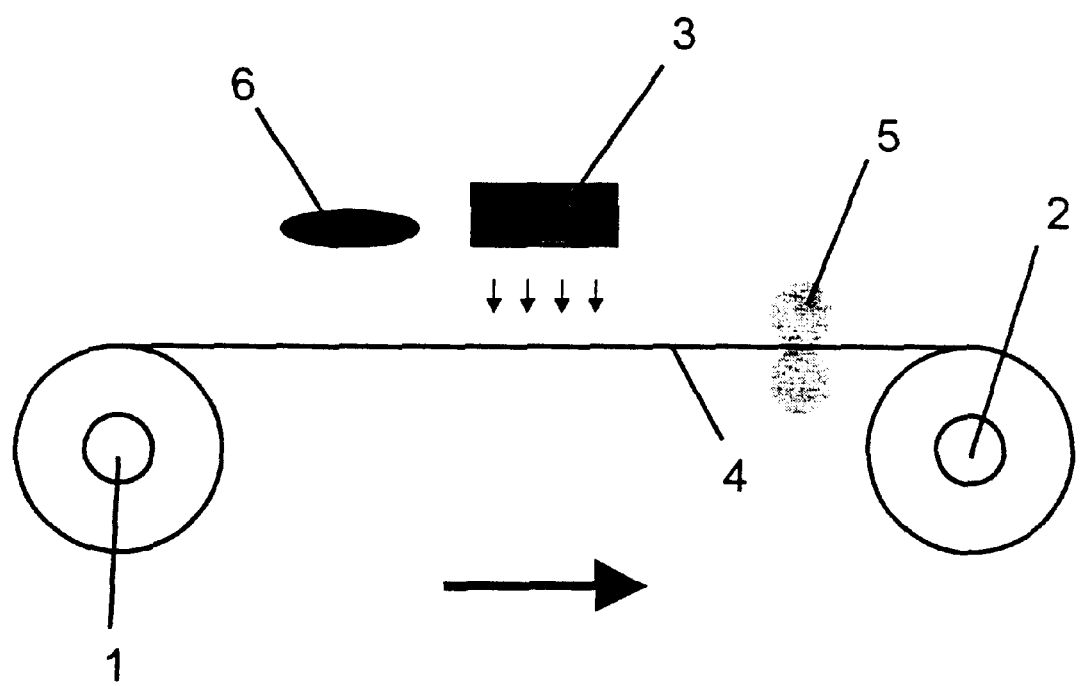

The invention relates to active substance plasters consisting of a backing material and an at least partially applied adhesive composition, the plaster comprising the active substance or, if desired, two or more active substances which are delivered to the skin, and to processes for producing the plasters.

Strongly adhering plasters are usually coated over their entire area with a zinc-rubber adhesive composition. The sticking of such products to the skin gives rise, following their removal, to marked skin irritation and to mechanical stressing of the skin. Without auxiliary means, it is impossible to break the bond painlessly.

In some cases, there are allergic reactions. Furthermore, the adhesive compositions used often lead to a transfer of composition onto the skin.

The use of skin-friendly adhesive compositions, such as acrylate adhesive compositions and hydrogels, is out of the question because of their low shear stability and tack. Improvement through aftertreatment, especially crosslinking, is possible, although the result remains unsatisfactory as a whole. The proprioreceptive effect is less than that of systems with a resin-rubber adhesive composition.

Other known adhesive systems based on conventional block copolymers are, on the one hand, not skin-friendly, owing to the high level of added stabiliser, or because of their high cohesiveness have been found suitable to date only for industrial applications, or, on the other hand, they cannot be formulated for strong adhesion and sticking to the skin.

The abovementioned adhesive compositions are pressure-sensitive self-adhesive compositions, it being possible for the compositions present in a carrier matrix for processing. The term carrier matrix is understood to refer to common organic or inorganic solvents or dispersion media.

Systems without a carrier matrix are referred to as 100% systems and are likewise not unknown. They are processed in the elastic or thermoplastic state. A common mode of processing is that of the melt. Pressure-sensitive hotmelt adhesive compositions of this kind have also already been described in the prior art. They are based on natural or synthetic rubbers and/or other synthetic polymers.

An advantage of the 100% systems is that they avoid the operation of removing the carrier matrix, i.e. the auxiliary means, thereby raising the productivity of processing and at the same time reducing the expenditure on machinery and the energy costs. In addition, this reduces the occurrence of residues of the carrier matrix, which, in turn, promotes a reduction in the allergenic potential.

Because of their high level of hardness, sticking to the skin is a problem for such 100% systems.

It is also known to apply such self-adhesive compositions not only over the entire area but also in the form of a pattern of dots, for example by screen printing (DE-C 42 37 252), in which case the dots of adhesive can also differ in their size and/or distribution (EP 0 353 972 B), or by intaglio printing of lines which interconnect in the longitudinal and transverse direction (DE-C 43 08 649).

The advantage of the patterned application is that the adhesive materials, given an appropriately porous backing material, are permeable to air and water vapour and, in general, are readily redetachable.

A disadvantage of these products, however, is that if the area covered by the adhesive layer, which per se is impermeable, is too large there is a corresponding reduction in the permeability to air and water vapour, and the consumption of adhesive composition rises; and also, if the area covered by the adhesive layer is small, the adhesion properties deteriorate, i.e. the product is detached too readily from the substrate, especially in the case of heavy, textile backing materials.

Transdermal therapeutic systems (TTS) are forms of administration of medicaments which deliver one or more medicaments to the skin over a defined period at their location of use. A distinction is made here between the systemic and local administration forms. With systemic administration forms, the active substance passes through the skin into the blood stream by diffusion and can act within the body as a whole. Local administration forms can, on the other hand, act only at the sites of application. The active substance remains in the skin or in the underlying layers.

Numerous embodiments of active substance plasters have already been described in the prior art, some of which operate in accordance with the reservoir principle, where the active substance is delivered, for example, via a membrane, in some cases also with a matrix system or with a relatively complex multilayer structure.

It is also known that the adhesive composition of the plaster can be employed as the matrix comprising the active substance. In addition to self-adhesive compositions applied from solution, hotmelt self-adhesive compositions have also been proposed for this purpose, as for example in EP 0 663 431 A, EP 0 452, 034 A, EP 0 305 757 A, DE-A 43 10 012, DE-A 42 22 334 and DE-C 42 24 325. The active substances listed in these documents, if named at all, are systemic ones.

As examples of active substance plasters, mention may be made of the active substance plasters which aid the circulation, belonging to the group of locally active therapeutic systems. The use of such plasters is indicated for the treatment of rheumatic complaints, sciatica, lumbago, stiff neck, shoulder/arm pain and muscular strains and sprains, muscular aching, or muscle, joint and nerve pain in the region of the locomotor system.

Capsaicin and nonivamide are known active substances in such locally acting, circulation-aiding plasters. Because of their use on the locomotor system they are in general required to adhere strongly. Usually, the plasters are coated over their whole area with a resin-rubber adhesive composition which comprises the active substance.

However, plasters of this kind, which usually have to be applied over a relatively large area, in some cases exhibit mechanical skin irritations after removal in the case of sensitive patients. After a prolonged period of application, their removal is to some extent painful.

A further disadvantage of the known thermally active plasters with an adhesive composition based on natural rubber which is applied in the form of a solution with organic solvents to the plaster backing is the comparatively low rate of release of the active substance.

The abovementioned disadvantages, and further disadvantages, apply also to active substance plasters comprising substances other than those mentioned.

For instance, WO 94/02123 describes an active substance plaster based on pressure-sensitive hotmelt adhesive compositions and comprising low-melting and/or readily volatile active substances in a concentration of from 2.5 to 25% by weight. The polymers employed in that document are A-B-A triblock styrene-ethylene-butylene-styrene block copolymers, which are notable for low initial tack and low bond strength on skin. The component comprising active substance is not spun.

EP 0 663 431 A2, EP 0 443 759 A3, EP 0 452 034 A2 and U.S. Pat. No. 5,371,128 describe uses of pressure-sensitive, silicone-based hotmelt adhesives with various additives and in differentiated structural forms. The component comprising active substance is not spun.

DE 43 10 012 A1 describes the structure of a dermal therapeutic system comprising meltable poly(meth)acrylate mixtures. The component comprising active substance is not spun.

DE 43 16 751 C1 describes a multi-chamber system for administering active substances. The component comprising active substance is not spun.

EP 0 439 180 describes an active substance plaster for administering tulobuterol. The component comprising active substance is not spun.

EP 0 305 757 describes an active substance plaster for administering nicotine. The component comprising active substance is not spun.

EP 0 305 758 describes an active substance plaster for administering nitroglycerine. The component comprising active substance is not spun.

EP 0 305 756 describes a device for dispensing substances, and the preparation and use thereof. The component comprising active substance is not spun.

DE 37 43 945 describes a device for delivering substances, and the production process. In the case of the pressure-sensitive hotmelt adhesive composition described, which is based on SIS, the device is not self-adhesive. The processing ranges indicated therein lie well below those of hotmelt adhesive compositions and for such described systems would not provide sufficient anchorage of the adhesive composition. The component comprising active substance is not spun.

WO 96/22083 indicates a polyisobutylene adhesive for transdermal purposes, which has a tackifier with a high glass transition point. The component comprising active substance is not spun.

The object of the invention was to provide active substance plasters which, while avoiding the disadvantages known from the prior art, feature a high level of efficacy, i.e. a relatively high rate of release, and good skin compatibility coupled with good adhesion. In addition, they should be able to be prepared in a technically simple and environmentally compatible manner.

This object is achieved by active substance plasters according to the main claim. The subclaims relate to advantageous embodiments of the plasters of the invention. The invention also embraces processes for producing such plasters.

The invention accordingly provides active substance plasters consisting of a backing material and an at least partially applied adhesive composition, which are notable in that a) a component comprising one or more active substances is additionally applied in the form of spun fibres or filaments to the backing material, this component b) having an at least partly thermoplastic basis.

The quantitative concentrations of the active substance or substances in the component lie preferably between 0.01 and about 60% by weight, particularly preferably from 0.1 to 50% by weight.

By active substances in the context of the present invention are meant chemical elements, organic and inorganic compounds which are able to migrate from the constituents of a generic device that comprise them and so bring about a desired effect. Among the fields of use of the device of the invention, human and veterinary medicine are of particular importance—in this case, an embodiment of the invention in plaster form is particularly preferred.

Typical substances which can be administered by way of devices produced in accordance with the invention are:

aceclidine, amfetaminil, amfetamine, amyl nitrite, apophedrine, atebrine, alprostadil, azulene, arecoline, anethole, amylene hydrate, acetylcholine, acridine, adenosine triphosphoric acid, L-malic acid, alimemazine, allithiamine, allyl isothiocyanate, aminoethanol, apyzine, apiole, azatadine, alprenolol, ethinazone, benzoyl peroxide, benzyl alcohol, bisabolol, bisnorephedrine, butacetoluide, benactyzine, camphor, colecalciferol, chloral hydrate, clemastine, chlorobutanol, capsaicin, cyclopentamine, clobutinol, chamazulene, dimethocaine, codeine, hlorpromazine, quinine, chlorothymol, cyclophosphamide, cinchocaine, hlorambucil, chlorphenesin, diethylethane, divinylethane, dexchlorpheniramine, dinoprostone, dixyrazine, ephedrine, ethosuximide, enallylpropymal, emylcamate, erythrol tetranitrate, emetine, enflurane, eucalyptol, etofenamate, ethylmorphine, fentanyl, fluanisone, guaiazulene, halothane, hyoscyamine, histamine, fencarbamide, hydroxycaine, hexylresorcinol, isoaminile citrate, isosorbide dinitrate, ibuprofen, iodine, iodoform, isoaminile, lidocaine, lopirine, levamisole, methadone, methyprylon, methylphenidate, mephenesin, methylephedrine, meclastine, methopromazine, mesuximide, nikethamide, norpseudoephedrine, menthol, methoxyfluran, methylpentinol, metixene, mesoprostol, oxy-tetracaine, oxyprenolol, oxyphenbutazone, oxyquinoline, pinene, prolintane, procyclidine, piperazine, pivazide, phensuximide, procaine, phenindamine, promethazine, pentetrazol, profenamine, perazine, phenol, pethidine, pilocarpine, prenylamine, phenoxybenzamine, Resochin, scopolamine, salicylic acid ester, sparteine, trichloroethylene, timolol, trifluoperazine, tetracaine, trimipramine, tranylcypromine, trimethadione, tybamate, thymol, thioridazine, valproic acid and verapamil, and also other active substances familiar to the skilled worker that can be absorbed through the skin, including mucosae. This list is of course not exhaustive.

Distribution of the active substances in the component takes place preferably in a thermal homogenizer, such as thermal mixers, thermal kneading apparatus, roll mills or screw systems, for example. The active substance can be added to the fully prepared component. By way of example, the active substance can also be incorporated into an intermediate stage or into the initial mixture.

The spun fibre or filament advantageously has a thickness of less than 300 $\mu$m, with particular preference between 0.1 and 250 $\mu$m.

In one preferred embodiment, the component is foamed and has a degree of foaming of at least 5% by volume, preferably from 10 to 75% by volume and, with particular preference between 40 and 60% by volume.

Furthermore, it has proved to be particularly advantageous for the component comprising active substance to be an adhesive composition, especially a self-adhesive composition. This adhesive composition can be identical to the adhesive composition used otherwise.

As adhesive compositions for the component comprising active substance and the components used otherwise, it is possible with advantage to employ thermoplastic hotmelt self-adhesive compositions based on natural and synthetic rubbers and on other synthetic polymers such as acrylates, methacrylates, polyurethanes, polyolefins, polyvinyl derivatives, polyesters or silicones with corresponding additives such as tackifier resins, plasticizers, stabilizers and other auxiliaries where necessary.

Their softening point should be higher than 50° C., since the application temperature is generally at least 90° C., preferably between 120° C. and 150° C. or between 180 and 220° C. in the case of silicones. If desired, subsequent crosslinking by irradiation with UV or electron beams may be appropriate.

Hotmelt self-adhesive compositions based on block copolymers, in particular, are notable for their diverse possibilities for variation, since by the controlled reduction of the glass transition temperature of the self-adhesive composition as a consequence of the selection of the tackifiers, of the plasticizers, and of the polymer molecule size and the molecular distribution of the starting components, the required bonding to the skin that is appropriate to the function is ensured even at critical points of the human locomotor system.

The high shear strength of the hotmelt self-adhesive composition is achieved by virtue of the high cohesiveness of the polymer. The good tack comes about as a result of the pallet of tackifiers and plasticizers that is employed.

For systems with particularly strong adhesion, the hotmelt self-adhesive composition is based preferably on block copolymers, especially A-B or A-B-A block copolymers or mixtures thereof. The hard phase A is ideally polystyrene or its derivatives, and the soft phase B comprises ethylene, propylene, butylene, butadiene, isoprene or mixtures thereof; of these, particular preference is given to ethylene and butylene or mixtures thereof.

However, polystyrene blocks may also be present in the soft phase B, in amounts of up to 20% by weight. The overall styrene content should, however, always be less than 35% by weight. Preference is given to styrene contents of between 5 and 30% by weight, since a lower styrene content makes the adhesive composition more conformable.

The controlled blending of diblock and triblock copolymers is particularly advantageous, preference being given to a diblock copolymer content of less than 80% by weight.

In one advantageous embodiment the hotmelt self-adhesive composition has the following composition:

| | |
|---|---|
| from 10 to 90% by weight | of block copolymers, |
| from 5 to 80% by weight | of tackifiers such as oils, waxes, resins and/or mixtures thereof, preferably mixtures of resins and oils, |
| less than 60% by weight | of plasticizers, |
| less than 15% by weight | of additives, |
| less than 5% by weight | of stabilizers, |
| less than 60% by weight | of active substance or substances, especially |
| 10% by weight | of active substance or active substances. |

The aliphatic or aromatic oils, waxes and resins used as tackifiers are preferably hydrocarbon oils, waxes and resins, the oils, such as paraffinic hydrocarbon oils, or the waxes, such as paraffinic hydrocarbon waxes, having a favourable effect on bonding to the skin by virtue of their consistency. Plasticizers used are medium- or long-chain fatty acids and/or their esters. These additives serve to establish the adhesive properties and the stability. If desired, further stabilizers and other auxiliaries are employed.

Filling the adhesive composition with mineral fillers, fibres and hollow or solid microbeads is possible.

The hotmelt self-adhesive compositions have a softening point of in particular more than 50° C., preferably from 70 to 220° C. and, with particular preference, from 75 to 140° C.

The hotmelt self-adhesive compositions are preferably formulated so that at a frequency of 0.1 rad/s they have a dynamic-complex glass transition temperature of less than 15° C., preferably from 6 to −30° C. and, with particular preference, from 3 to −25° C.

Plasters in particular are subject to stringent requirements in terms of the adhesion properties. For ideal application the hotmelt self-adhesive composition should possess a high tack. There should be functionally appropriate bond strength to the skin and to the reverse of the backing. So that there is no slipping, the hotmelt self-adhesive composition is also required to have a high shear strength.

The controlled reduction of the glass transition temperature of the self-adhesive composition as a consequence of the selection of the tackifiers, of the plasticizers and of the polymer molecule size and the molecular distribution of the starting components achieves the required functionally appropriate bonding to the skin and to the reverse of the backing. The high shear strength of the self-adhesive composition employed here is achieved by virtue of the high cohesiveness of the block copolymer. The good tack comes about through the range of tackifiers and plasticizers that is employed.

Product properties such as tack, glass transition temperature and shear stability can be quantified readily using a dynamomechanical frequency measurement. In this case, use is made of a rheometer controlled by shearing stress.

The results of this measurement method give information on the physical properties of a substance by taking into account the viscoelastic component. In this context, at a defined temperature, the hotmelt self-adhesive composition is placed in oscillation between two plane-parallel plates with variable frequencies and low deformation (linear viscoelastic range). Via a pickup control unit, with computer assistance, the quotient ($Q = \tan \delta$) between the loss modulus ($G''$, viscous component) and the storage modulus ($G'$, elastic component) is determined.

$$Q = \tan \delta = G''/G'$$

A high frequency is chosen for the subjective sensing of the tack and a low frequency for the shear strength. A high numerical value denotes better tack and poorer shear stability.

The complex-dynamic glass transition point is the transition point from the amorphous to the viscoelastic range. It corresponds to the maximum of the temperature function at a defined frequency.

| Designation | $T_g$ low frequency | Conformability low frequency/RT | Tack high frequency/RT |
|---|---|---|---|
| Hotmelt self-adhesive composition A | −12 ± 2° C. | tan δ = 0.08 ± 0.03 | tan δ = 0.84 = 0.03 |
| Hotmelt self-adhesive composition B | −9 ± 2° C. | tan δ = 0.22 ± 0.03 | tan δ = 1.00 = 0.03 |

Preference is given in accordance with the invention to hotmelt self-adhesive compositions for which the ratio of the viscous component to the elastic component at a frequency of 100 rad/s at 25° C. is greater than 0.6, or to hotmelt self-adhesive compositions for which the ratio of the viscous component to the elastic component at a frequency of 0.1 rad/s at 25° C. is less than 0.6, preferably between 0.35 and 0.02 and, with very particular preference, between 0.3 and 0.1.

As a preferred process for the coating—open-pored in accordance with the invention—of air-permeable and water vapour-permeable doped adhesive layers it is possible to employ the spinning technology for applying thermoplastics and adhesives.

The contactless coating and application of hotmelt self-adhesive compositions by spinning with compressed air or inert gases is already widely employed.

With stringent requirements on uniformity and low weight per unit area, however, there are narrow limits for the coating at high viscosities. Especially when applying adhesives with a relatively high viscosity of more than 10 Pa*s, a tendency towards severe "blobbing" appears. On the basis of fundamental scientific research into spinning jet theory, therefore, special spinning techniques have been developed for thermoplastics of relatively high viscosity (high molecular mass).

Using the melt spin, Acufiber and Durafiber processes it is nowadays possible to process thermoplastics in the pressure-sensitive sector up to 2000 Pa*s at 200° C. Therefore, a range of application possibilities in the sector of the spinning of thermoplastic adhesives is possible.

The advantages of this application technique, such as contactless, geometry-independent coating coupled with low thermal loading of the backings, opens up access to completely new plaster specialities.

The multiplicity of techniques are described by way of example by Acumeter, J+M Laboratories, Dynafiber and ITO Dynatex Nordson. Common to all of them are the flow processes in the spinning nozzles. Melted thermoplastics are among the group of non-newtonian liquids with pseudoplastic flow behaviour, i.e., shearing stress and coating speed are not in linear correlation with one another. The thermoplastic polymers most commonly used as hotmelt adhesives consist of linear and/or branched chain molecules. In the course of the process of aerodynamic stretching, the flow rate increases at the spun filament and the molecules become more and more disentangled and orient themselves in the flow direction.

For this reason, all nozzles utilize an internal mixing principle in which the adhesives are already surrounded by a flow of compressed air within the nozzle chamber. The narrowest gap is therefore the nozzle outlet. The outlet gap here can be circular or slot-shaped. If this spun filament is sprayed onto a substrate, the result is a random-laid nonwoven with an intrinsically linked structure. The random-laid nonwoven consists of a disordered, homogeneous arrangement of a looped continuous filament.

The doped adhesive layer, applied contactlessly via an arbitrary series of nozzles, dependent on the coating width, and spun in a weblike manner has a much higher free surface area than do full-area coatings. In contact with the skin, different release properties or release kinetics of the respective active substances and, if appropriate active-substance combinations are to be expected.

The controlled exertion of influence over, or change/increase in, the release properties is to be expected as a result of doped hotmelt pressure-sensitive adhesive coatings spun in a weblike manner, since the adhesive matrices doped over their entire area exhibit generally diffusion-controlled release characteristics.

In the text below, apparatus for producing plasters according to the invention will be explained with reference to a number of figures.

BRIEF DESCRIPTION OF DRAWINGS

FIG. 1, shows the mechanical components involved in the assembly method of the claimed and disclosed plaster.

FIG. 2, shows a modification of the method of FIG. 1, in that two spin nozzles are employed to apply more than one type of spun fiber.

FIG. 3, demonstrates further modifications of the basic method depicted in FIG. 1, wherein a corona-treatment station and/or a calendaring station are added.

In the simplest case in accordance with FIG. 1, the apparatus consists of an unwinder (1) and winder (2) and the backing web (4) and the spin nozzle (3).

In order to optimize the properties it is also possible to employ a series of two or more nozzles, in accordance with FIG. 2.

For special backings, a corona pretreatment (6) or subsequent calendering station can be included in the experimental set-up, as is shown in FIG. 3.

Doped layers spun in a netlike manner will, owing to their open structure, exhibit a more surface-controlled release, especially if intimate wetting of the contact areas is able to take place as a result of moisture from the body itself or from outside.

The interaction of the active substances with the skin is, as is known, modulated by enhancers that are mixed into the adhesive composition or intensified by the occlusive effect of adhesive composition and covering. In contrast to this it is possible, through the use of breathable doped coatings in conjunction with elastic and likewise breathable backing materials, in particular for example during sporting activities, to achieve a) a level of wear comfort which is perceived subjectively as more pleasant by the user, and b) as a result of an interaction of the skin with the environment (for example, suppression of perspiration) that is less disturbed by the release behaviour, a more defined penetration of active substances into the skin.

In contrast, by virtue of the processes mentioned here, it is also possible to achieve permeability of the doped plaster system from the outside. Owing to this property of the product, therefore, it is possible following actual application for substances to be brought to the contact point between doped adhesive/skin, from outside through the backing, even at later times (sprinkling on of liquid, wiping, etc.). These substances might, for example, comprise an additional enhancer effect or might initiate or attenuate the pharmaceutical action or modulate it appropriately for a favourable response for the consumer.

In addition to this, the spinning process also offers some technical possibilities for the use of partial coatings of doped hotmelt pressure-sensitive adhesives:

- through the selection of individual nozzles in the series of application nozzles which is arranged transversely to the backing, the active substance only, with a suitable carrier medium, can be applied in a controlled manner. This is advantageous insofar as any incompatibilities of an active substance with an adhesive matrix are avoided and a doped plaster can be optimized in accordance with bond strength and medicament activity not until a very late point in time directly during the coating operation.
- Active substances can in principle also be applied partially and contactlessly to a backing which is already provided with an adhesive layer, in which case the choice of the backing and of the form of coating (partial/complete) is free.
- The separation of the coating elements into components which come into contact with active substance, and other components, offers the further advantage of a GMP-compliant configuration of the coating unit. This is made possible through modular replacement and separate cleaning of only limited parts of the equipment (for example, use of individual nozzles in the form of "dedicated equipment").

In one particular embodiment the adhesive composition is foamed. For specific applications, this must ensure the functionally appropriate use of the plasters.

Here, the adhesive compound provided with the active substances is foamed preferably using inert gases such as nitrogen, carbon dioxide, noble gases, hydrocarbons or air, or mixtures thereof. In some cases, foaming additionally by thermal decomposition of gas-evolving substances such as azo, carbonate and hydrazide compounds has been found to be suitable.

The degree of foaming, i.e. the gas content, should be at least 5% by volume and can range up to about 85% by volume. In practice, values of from 10 to 75% by volume, preferably 50% by volume, are well established. Operating at relatively high temperatures of approximately 140° C. and a comparatively high internal pressure produces very open-pored adhesive foam layers whose permeability to air and water vapour is particularly good. The advantageous properties of the adhesive coatings of the invention, high tack and good conformability even to uneven surfaces owing to the elasticity and plasticity of the foamed adhesive compositions, and the initial tack, can be utilized optimally in the field of active substance plasters.

At the same time, owing to the vacuoles in the foam, the transport of certain active substances is increased by a more than proportional amount, and so very good release rates are achieved.

A particularly suitable process for producing the adhesive composition foamed in accordance with the invention operates in accordance with the foam-mix system. In this system, the thermoplastic adhesive composition is reacted with the intended gases, such as nitrogen, air or carbon dioxide, for example, in various volume proportions (from about 10 to 80% by volume) in a stator/rotor system under high pressure and at a temperature above the softening point (approximately 120° C.). While the gas entry pressure is greater than 100 bar, the mixing pressures between gas and thermoplastic in the system are from 40 to 100 bar, preferably from 40 to 70 bar. The pressure-sensitive adhesive foam produced in this way can subsequently pass through a line into the applicator unit. In the applicator unit, commercially customary nozzles, screen systems or chamber systems are used.

The foamed adhesive compound is then applied to a backing material by way of the process described above. Here, an open-pored coating is achieved of doped layers of regulated permeability to air and water vapour, which are suitably produced by way, for example, of the melt-spin process or Durafiber process.

The foaming of the adhesive compound considerably reduces the applied amount required without adversely affecting the other properties.

Foaming, moreover, generally lowers the viscosity of the adhesive compositions. This reduces the melt energy, and it is also possible to coat thermally unstable backing materials directly.

The component comprising active substances is preferably applied with a weight per unit area of more than 15 g/m$^2$, preferably between 30 and 500 g/m$^2$ and, with very particular preference, between 90 and 400 g/m$^2$, to the backing material.

Suitable backing materials are all rigid and elastic sheetlike structures made from synthetic and natural raw materials. Preference is given to backing materials which following application of the adhesive composition can be employed such that they meet the properties required of a functionally appropriate bandage. By way of example, mention may be made of textiles such as wovens, knits, lays, nonwovens, laminates, nets, and also films, foams and papers. In addition, these materials may be pretreated and/or aftertreated. Common pretreatments are corona and hydrophobicization; customary aftertreatments are calendering, thermal conditioning, laminating, punching and sheathing and crosslinking.

Depending on the backing material and its temperature sensitivity, the foamed hotmelt self-adhesive composition can be applied directly, or can be applied first to an auxiliary backing and then transferred to the final backing.

The adhesive composition applied in addition to the component is advantageously applied partially to the backing material, in particular by means of halftone printing, screen printing, especially thermal screen printing, thermal flexographic printing or intaglio printing, especially gravure printing, or by spraying.

The percentage area coated with the adhesive composition should be at least 10%, preferably from 40 to 60% and, with very particular preference, from 70 to 95%.

Subsequent calendering of the coated product and/or pretreatment of the backing, such as corona irradiation, to improve anchoring of the adhesive layer, may also be advantageous.

Furthermore, treating the foamed hotmelt self-adhesive composition by electron beam postcrosslinking or UV irradiation may lead to an improvement in the desired properties.

The backing material coated with the spun polymer composition can have an air permeability of more than 1 cm$^3$/(cm$^2$*s), preferably greater than 15 cm$^3$/(cm$^2$*s) and, with very particular preference, greater than 70 cm$^3$/(cm$^2$*s), and a water vapour permeability of more than 500 g/(m$^2$*24h), preferably more than 1000 g/(m$^2$*24h) and, with very particular preference, more than 2000 g/(m$^2$*24h).

Finally, following the coating operation, the material can be lined with a repellent backing material, such as siliconized paper, or with a wound pad or padding. Subsequently, the plasters are punched out in the desired size.

It is particularly advantageous for the material to be sterilizable, preferably sterilizable by means of γ (gamma) radiation. Therefore, hotmelt self-adhesive compositions on a block copolymer basis, containing no double bonds, are particularly suitable for subsequent sterilization. This applies in particular to styrene-butylene-ethylene-styrene or styrene-butylene-styrene block copolymers. In this case, no changes in the adhesion properties which are significant for the utility occur.

The plaster of the invention can have a bond strength to the reverse of the backing of at least 0.5 N/cm, in particular a bond strength of between 1.0 and 6.0 N/cm. On other substrates, higher bond strengths may be achieved.

In the text below, particularly advantageous plasters of the 20 invention will be described without any intention thereby to restrict the invention unnecessarily.

EXAMPLE

In accordance with the invention, a substance release device was produced which comprises a hyperaemic active substance. On the basis of its properties as described below, the device can be used for application as a rheumatic plaster which in addition, on the basis of the good adhesion properties, can be applied for a number of days to joints of the human locomotor system. The backing material consisted of a nonelastic woven cotton fabric having a maximum tensile strength of more than 80 N/cm and an extension at maximum tension of less than 20%.

The composition of this hotmelt pressure-sensitive adhesive composition was as follows:

an A-B/A-B-A block copolymer consisting of hard and soft segments, with an A-B-A:A-B ratio of 3:7 and a styrene content in the polymer of 30 mol %; its proportion in the adhesive composition is 32% by weight (Kraton G)

a paraffinic hydrocarbon wax whose proportion in the adhesive composition is 52% by weight hydrocarbon resins, with a proportion of 14.5% by weight (Super Resin HC 140)

an ageing inhibitor, with a proportion of less than 0.5% by weight (Irganox 1010)

a hyperaemic active substance (nonyl vanillamide), with a proportion of 1%.

The adhesive components employed were homogenized in a thermal mixer at 185° C. for 3 h. The active substance was added in the cooling phase at 140° C., and homogenization was continued in the mixer for 40 minutes.

The softening point of this adhesive composition was about 80° C. (DIN 52011) and the adhesive composition had a viscosity of 2100 mPas at 150° C. (DIN 53018, Brookfield DV II, spindle 21). The glass transition by the above method was −9° C.

The doped hotmelt adhesive composition prepared in this way was applied to the backing using a Dynafiber spray nozzle. The direct coating operation took place at 10 m/min and at a temperature of 120° C. The backing material was coated at 170 g/m².

The plaster material produced in this way shows good release of active substance (release study). After 24-hour application in vitro on pigskin, 15% of the plaster charge had been absorbed dermally.

The air permeability of the open-pored treated backing material was 25 cm³/cm²*s). Following application, no instances of skin irritation were found.

What is claimed is:

1. Active substance plaster comprising a backing material and an adhesive composition, wherein,
   a) the adhesive composition is in the form of fibers or filaments, said fibers or filaments further comprising a mixture of foamed adhesive and at least one active substance,
   b) the adhesive composition comprises at least one thermoplastic component, and
   wherein the percentage of the backing material's surface area to which the adhesive composition is applied is less than 100%.

2. Active substance plasters according to claim 1, wherein that the comporent comprises the active substance in an amount of from 0.01 to 60% by weight.

3. Active substance plasters according to clalm 1, wherein the fibre or the filament has a thickness of less than 300 μm.

4. Active substance plasters according to claim 1, wherein the component is foamed and has a degree of foaming of at least 5% by volume.

5. Active substance plasters according to claim 1, wherein the component comprising active substance is an adhesive composition.

6. Active substance plasters according to claim 1, wherein the adhesive composition is a hotmelt self-adhesive composition composed on the basis of synthetic rubbers selected from the group consisting of block copolymers, acrylates, methacrylates, polyurethanes, polyolefins, polyvinyl derivatives, polyatrylamides, polyesters and silicones.

7. Active substance plasters according to claim 6, wherein said hotmelt self-adhesive composition is composed on the basis of A-B or A-B-A block copolymers or mixtures thereof, phase A being primarily polystyrene or its derivatives and phase B being ethylene, propylene, butylene, butadiene, isoprene or mixtures thereof.

8. Active substance plasters according to claim 6, wherein the hotmelt self-adhesive composition comprises

| a) from 10 to 90% by weight | of block copolymers, |
|---|---|
| b) from 5 to 80% by weight | of tackifiers in a form selected from the group consisting of oils, waxes, resins and/or mixtures thereof, |
| c) less than 60% by weight | of plasticizers, |
| d) less than 15% by weight | of additives, |
| e) less than 5% by weight | of stabilizers, and |
| f) less than 10% by weight | of active substance or substances. |

9. Active substance plasters according to claim 1, wherein the component comprising active substance is applied with a weight per unit area of more than 15 g/m² to the backing material.

10. Active substance plasters according to claim 1, wherein the adhesive composition applied additionally to the component is applied partially by means of halftone printing, screen printing, thermal flexographic printing or intaglio printing, or by spraying.

11. Active substance plasters according to claim 1, wherein the percentage of the backing material's surface area to which the adhesive composition is applied is at least 10%.

12. Active substance platers according to claim 1, wherein the plaster is sterilizable by means of a γ (gamma) radiation.

13. Active substances plasters according to claim 1, obtained by the spinning process.

14. The active substance plaster of claim 2, wherein said amount of said active substance if from 0.1 to 60% by weight.

15. The active substance plaster of claim 3, wherein said thickness is from 0.1 to 250 μm.

16. The active substance plaster of claim 4, wherein said degree of foaming is from 40 to 60% by volume.

17. The active substance plaster of claim 5, wherein said active substance is a self-adhesive composition.

18. The active substance plaster of claim 6, wherein phase A is selected from the group consisting of ethylene, butylene and their mixtures.

19. Active substance plaster according to claim 9, wherein said component is applied to an amount of 90 to 400 g/m².

20. Active substance plaster of claim 11, wherein said percentage area that is coated is from 70 to 95%.

21. The active substance plaster of claim 13, wherein said spinning process is a melt-spin technique or the Durafiber technique.

22. Active substance plasters according to claim 1, wherein the tackifier is at least one oil, wax, resin or mixtures thereof.

23. Active substance plasters according to claim 5, wherein the tackifier is a mixture of at least one resin and at least one oil.

24. Active substance plasters according to claim 1, wherein, the at least one active substance is from 0.1 to 50% by weight of the fiber or filament containing it.

25. Active substance plasters according to claim 1, wherein the at least one the first or second adhesive composition is foamed and has a degree of foaming of from 10 to 75% by volume.

26. Active substance plasters according to claim 1, wherein the at least one the first or second adhesive composition is foamed and has a degree of foaming of from 40 to 60% by volume.

27. Active substance plasters according to claim 7, wherein the block copolymers comprising the hotmelt self-adhesive composition is composed of A-B or A-B-A block copolymers, or mixtures thereof, wherein phase A comprises a polystyrene or at least one derivatives thereof, and phase B comprises ethylene, propylene, butylene, butadiene, isoprene or mixtures thereof.

28. Active substance plasters according to claim 8, wherein the tackifier comprises mixtures of resins and oils.

29. Active substance plasters according to claim 9, wherein the fiber or filament having the at least one active agent is applied to the backing material with a weight between 30 and 500 g/m$^2$.

30. Active substance plasters according to claim 1, wherein the percentage of the backing's surface area that is coated with adhesive composition is from 40 to 60%.

31. Active substance plasters according to claim 1, wherein the fibers or filaments further comprise one or more distinct groups of fibers or filaments, wherein at least one of the groups is compositionally distinct with respect to either (i) the at least one active substance or (ii) the adhesive composition, or both (i) and (ii).

32. Active substance plasters according to claim 31, wherein at least one of said groups of fibers or filaments comprises the second adhesive composition.

33. Active substance plasters according to claim 31, wherein at least one group of fibers or filaments contains at least one different active substance than those contained by at least one other group of fibers or filaments.

34. Active substance plasters according to claim 31, wherein at least one group of fibers or filaments comprises at least one different adhesive component than those contained by at least one other group of fibers or filaments.

35. Active substance plasters according to claim 1, wherein a portion of the adhesive-containing fibers do not comprise any active agent.

36. Active substance plasters according to claim 1, wherein the fiber or filament having the at least one active agent is applied to the backing material so as to allow said fiber or filament to be in direct contact with the skin of the plaster user.

* * * * *

UNITED STATES PATENT AND TRADEMARK OFFICE
CERTIFICATE OF CORRECTION

PATENT NO. : 6,656,491 B1
DATED : December 2, 2003
INVENTOR(S) : Brosck et al.

It is certified that error appears in the above-identified patent and that said Letters Patent is hereby corrected as shown below:

Column 11,
Line 58, "comporent" should read -- component --
Line 60, "clalm 1" should read -- claim 1 --

Column 12,
Line 6, "polyatrylamides" should read -- polyacrylamides --
Line 44, "0.1 to 60%" should read -- 0.1 to 50% --

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,656,491 B1 Page 1 of 1
DATED : December 2, 2003
INVENTOR(S) : Brosck et al.

It is certified that error appears in the above-identified patent and that said Letters Patent is hereby corrected as shown below:

Column 12,
Line 44, "if" should read -- is --

Signed and Sealed this

Fifth Day of April, 2005

JON W. DUDAS
*Director of the United States Patent and Trademark Office*